United States Patent [19]

Schlager

[11] Patent Number: 4,882,492

[45] Date of Patent: Nov. 21, 1989

[54] NON-INVASIVE NEAR INFRARED MEASUREMENT OF BLOOD ANALYTE CONCENTRATIONS

[75] Inventor: Kenneth J. Schlager, Elm Grove, Wis.

[73] Assignee: Biotronics Associates, Inc., Wauwatosa, Wis.

[21] Appl. No.: 145,459

[22] Filed: Jan. 19, 1988

[51] Int. Cl.$^4$ .................. G01N 33/50; G01N 21/59; G01N 21/47

[52] U.S. Cl. .................. 250/346; 250/341; 250/345; 356/39

[58] Field of Search ............... 128/633; 356/39, 40, 356/41; 250/345, 343, 346, 341

[56] References Cited

U.S. PATENT DOCUMENTS

| | | | |
|---|---|---|---|
| 1,758,088 | 5/1930 | Schmick | 250/346 |
| 2,721,942 | 10/1955 | Friel et al. | 250/343 |
| 3,926,527 | 12/1975 | Pembrook et al. | 250/339 |
| 4,655,225 | 4/1987 | Dähne et al. | 128/633 |

*Primary Examiner*—Carolyn E. Fields
*Attorney, Agent, or Firm*—Andrus, Sceales, Starke & Sawall

[57] ABSTRACT

A non-invasive apparatus and related method for measuring the concentration of glucose or other blood analytes utilizes both diffuse reflected and transmissive infrared absorption measurements and may be applied to either in vitro or in vivo sampling. The apparatus and method utilize non-dispersive correlation spectrometry and apply it to liquid blood serum analysis. Spectrally-modified near infrared light from the sample containing the analyte is split into two beams, one of which is directed through a negative correlation filter which blocks light in the absorption bands for the analyte to be measured, and the other of which is directed through a neutral density filter capable of blocking light equally at all wavelengths in the range of interest. Differencing the light intensity between the two light paths provides a measure proportional to analyte concentration.

21 Claims, 1 Drawing Sheet

NON-INVASIVE NEAR INFRARED MEASUREMENT OF BLOOD ANALYTE CONCENTRATIONS

BACKGROUND OF THE INVENTION

The present invention is directed to an apparatus and method of its use for determining non-invasively the concentrations of certain blood analytes. More particularly, the invention is directed to a low cost apparatus intended for home use by diabetics to monitor and measure blood glucose levels.

Persons suffering from diabetes may typically monitor their own glucose concentrations with periodic daily measurements, usually four times each day. Present methods require the diabetic to draw a blood sample for each test and to use a chemical reagent in the test procedure for measuring glucose concentration. Blood extractions for such tests often become a real burden to the diabetic and, in addition, the chemical reagents used in the tests are quite expensive, particularly in view of the large number of tests required. Therefore, a simple and accurate method and apparatus for non-invasively measuring glucose concentration would be most desirable. Further, such an apparatus which could be supplied at relatively low cost and used by a diabetic at home, in place of present invasive techniques, is particularly desirable.

Various kinds of apparatus and related methods for the non-invasive determination of glucose concentrations, as well as concentrations of other blood analytes, are known in the art. European Pat. Application No. 84840212, filed May 4, 1984 (Publication No. 0160768, dated Nov. 13, 1985) describes such an apparatus and its method of use. The described method uses dispersive technology in which a monochromator directs two or more separate wave lengths of light into body tissue, either transmissively or reflectively, for individual glucose absorbance measurements. A microprocessor then calculates the glucose concentration from the series of such absorbance measurements. The techniques and apparatus described in the above identified application are typical of the traditional methods of near infrared analysis based on the measurement of absorbance at a single or multiple specific wavelengths.

Non-invasive, in vivo monitoring of oxidative metabolism, utilizing both transmissive and diffuse reflective methods, is disclosed in U.S. Pat. Nos. 4,281,645 and 4,223,680, respectively. However, both patents describe techniques utilizing the measurement of infrared light absorbance at specific individual wavelengths.

The concentrations of certain major blood compounds, such as glucose and cholesterol, are much lower than concentrations of compounds typically analyzed by near infrared spectrometry. Glucose concentration averages only about 0.1% by weight (1000 ppm) of blood serum. Furthermore, an accuracy of ±50 ppm is required for any meaningful measurement of concentration. Thus, sensitivity to IR absorption measurements has traditionally been a problem in determining glucose concentration. Another problem concerns the existence of other blood serum components which compete with glucose as light absorbers in the near infrared spectral region where glucose is moderately or strongly absorbing. Thus, interference from such competing components as proteins and water has typically been a problem. In addition, the concentrations of serum proteins are significantly higher than glucose in the spectral regions of interest, thereby compounding the interference problem.

It is also recognized that there are practical limits on the spectral bandwidth in the near infrared region which can be used for meaningful glucose measurements and that reflective and transmissive measurements cannot both be used effectively over that bandwidth. At wavelengths less than about 900 to 1,000 nm (nanometers), other strongly absorbent materials also exist and the specific absorption due to glucose may be too small to provide the necessary sensitivity and accuracy, particularly in view of the interfering absorbers. In the range of 1000 to 1800 nm, glucose absorption is somewhat improved, but still relatively low. IR absorbence by glucose in the range of 1800 to 2800 nm is much greater and, at least theoretically, higher absorbance in this range should provide sufficient sensitivity to accurately measure glucose concentrations. However, at wavelengths greater than 1800 nm, light is strongly absorbed by water and has little penetration capability into glucose-containing tissue, despite the high specific absorption by glucose at these wavelengths. As a result, transmissive measurements in the region above about 1800 nm are impractical.

Non-dispersive correlation spectrometry, utilizing a relatively wide infrared spectral band, has long been used in gas analysis, such as engine gas emission analysis. A gas-filter correlation spectrometer correlates spectral absorption signals from the gas being measured and a gas in a filter. In particular, systems utilizing a so-called "negative filter" have been found to be particularly effective and exhibit a low sensitivity to interfering gases. One such system is described in Cha and Gabele, "Study on Infrared Gas-Filter Correlation Spectrometer for Measuring Low-Concentration Methanol Gases", Optical Engineering, Volume 25, No. 12, pages 1299–1303 (December 1986). However, gas filters used in gas correlation cells are relatively easy to make and use. A gas correlation cell typically comprises a sealed glass or plastic cell that contains the gas of interest at a predetermined concentration. A liquid correlation cell, on the other hand, is much more difficult to design, make and use and, to applicant's knowledge, the principles of gas filter correlation spectrometry have not been applied to liquid analysis.

There is a particular need today for a non-invasive instrument which could be used by the diabetic at home for measuring and monitoring glucose levels. Such a device would eliminate the need for chemical tests requiring expensive reagents, as well as the burden and trauma associated with multiple daily blood sampling. The device should also be relatively low in cost and, ideally, be less than the annual cost of current invasive methods.

SUMMARY OF THE INVENTION

The present invention is directed broadly to an apparatus and related method for the non-invasive measurement of blood analyte concentration utilizing non-dispersive near infrared correlation spectrometry. The apparatus and method are particularly adaptable to the measurement of glucose concentration, but may be applied to measuring the concentration of a number of blood analytes. The apparatus and method are adapted to utilize either transmissive or diffuse reflective measurements.

A source of modulated light in the near infrared bandwidth is transmitted to a source containing the blood analyte. The light is either reflectively or transmissively modified by the source and the spectrally-modified light is retransmitted to a beam splitter to provide two beams for the correlation analysis. One beam is directed to a correlation cell which functions as a negative optical filter by providing an absorption spectra for the analyte at a level sufficient to block light over the selected bandwidth for the expected concentration range of the analyte. The other beam is directed to a reference cell, in the form of a neutral density filter, which has an absorption spectra sufficient to block light equally at all wavelengths in the selected bandwidth. The intensities of each of the beams are measured by a photosensor and a signal representative of the difference in the beam intensities, which is proportional to the analyte concentration, is generated and converted into a direct indication of analyte concentration.

In the preferred embodiment of the apparatus, for measuring glucose concentration, a non-dispersed band of near infrared light is transmitted via a fiber optic link to the skin surface of the tissue to be analyzed. The light is directed to be diffusely reflected from the skin surface and the spectrally-modified light is divided by a beam splitter. The negative correlation filter comprises glucose in a non-absorbing solvent or a coating of glucose solution on a glass substrate.

Utilizing diffusely reflective measurement allows operation in a selected bandwidth where glucose absorbance is much higher (in the range of above about 1800 nm). Necessary sensitivity for accurate glucose measurement exists in this range, and sensitivity is substantially improved with non-dispersive techniques in which IR absorbance information over the entire bandwidth may be used.

DETAILED DESCRIPTION OF THE PREFERRED EMBODIMENT

Figure 1:
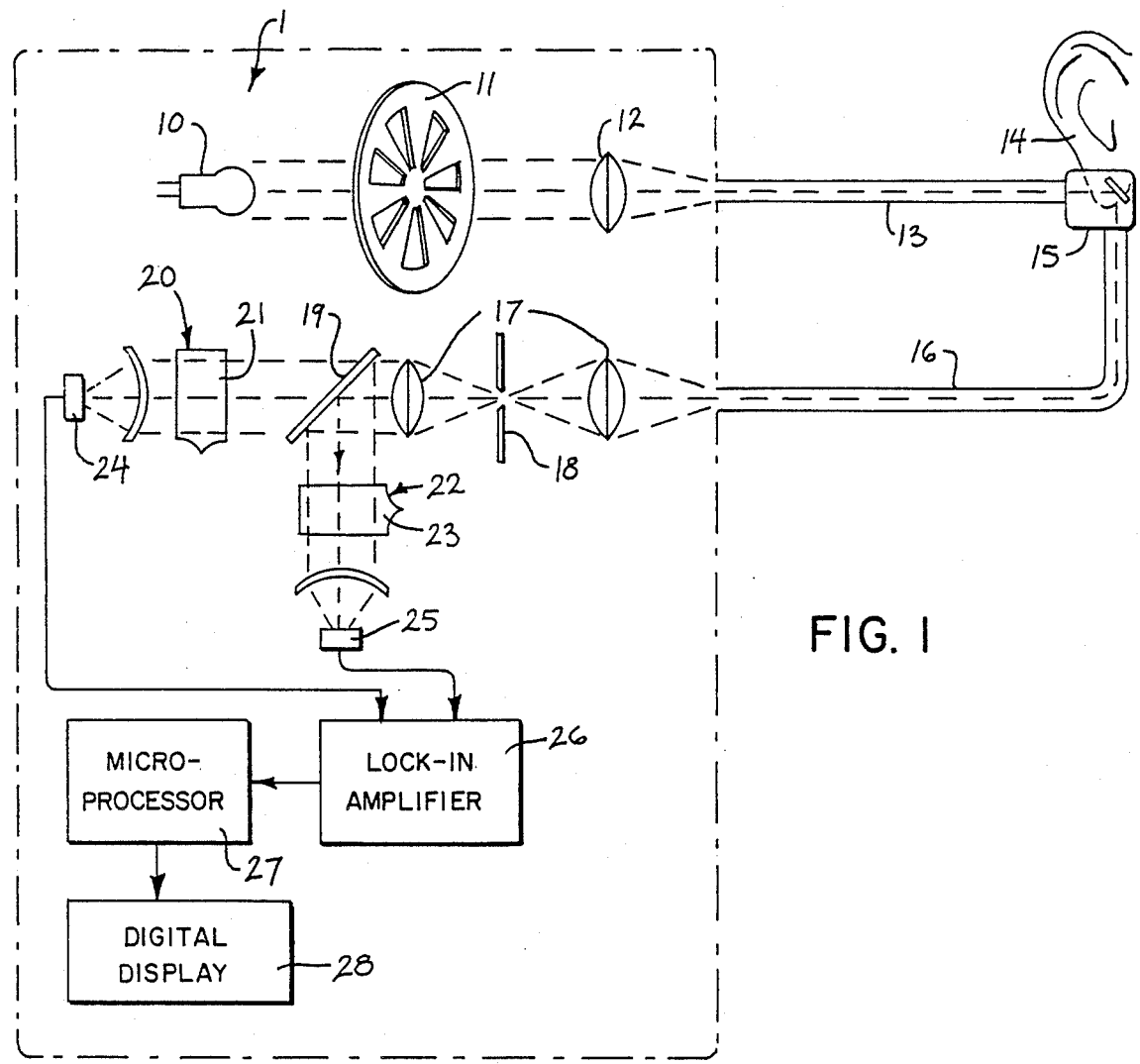
FIG. 1 is a schematic representation of the apparatus of the preferred embodiment of the present invention.

An apparatus for the non-invasive infrared analysis of blood chemistry is shown in FIG. 1. It will be hereinafter described with respect to construction and use in its preferred embodiment for the measurement of glucose concentration. A spectrometer 1 includes a light source in the form of a tungsten halogen lamp 10 which generates a spectrum of light in the visible and near infrared regions. The light from the lamp 10 is first modulated by passing it through a chopper wheel 11 to provide light signals which can be processed to minimize background noise resulting from ambient light and other stray signals. The light is then focused by a lens 12 into a fiber optic transmission cable 13 where it is directed to the source of the analyte, i.e. glucose, to be measured. As shown in FIG. 1, the glucose source is blood within the tissue of an ear lobe 14.

The light carried in the fiber cable 13 may be transmitted through the ear lobe 14 or it may be caused to impinge on the skin surface of the tissue (such as a patient's arm) at an angle where it is absorbed by tissue material near the surface and reflected as diffuse radiation. In either case, the light is spectrally-modified as a result of infrared absorption by the blood and tissue components, including glucose. In the apparatus shown, an optrode 15 at the end of the fiber cable 13 transmits light energy to the skin surface, receives the spectrally-modified light transmitted through the tissue, and retransmits it into the reception fiber optic cable 16. The spectrally-modified light is then returned to the spectrometer 1 through a pair of lenses 17 separated by a slit 18 which aids in rejecting stray light.

In the embodiment utilizing diffuse reflectances, a near infrared bandwidth in the range of 1800 to 3400 nm is preferred. Glucose is known to be much more strongly absorbing in this range but, because of the similar high absorbance by water in this region, transmissive measurements are not practical. Serum proteins, which exist in signficantly higher concentrations than glucose in the near infrared spectral regions of interest, constitute a serious source of interference, particularly when measuring transmissively. However, human skin layers act as a natural filter that allow smaller glucose molecules to move to the surface, but restrict movement thereto of the larger protein molecules. Therefore, reflective skin surface measurements are less subject to protein interference than are transmissive measurements. Furthermore, a correlation between skin surface glucose and serum glucose has been established and direct measurement of the former can be converted into the latter.

The light exiting lens 17 is directed through a beam splitter 19. One of the modified light beams from the splitter is directed through a correlation cell 20 comprising a negative correlation filter 21. The correlation filter contains a glucose absorption spectra sufficient to block light for the maximum anticipated concentration of glucose in the tissue sample. The correlation filter may comprise an aqueous solution of glucose at a predetermined concentration. Such water solutions are preferred because they simulate blood absorption. However, water solutions of glucose are often unstable. The negative correlation filter 21 may also comprise a non-aqueous glucose solution, using a non-absorbing solvent. Alternatively, the filter may comprise a coating of a glucose solution on a glass substrate. In the two latter cases, a separate layer of water is also used to simulate water absorption in the blood.

The other modified split beam is directed through a reference cell 22 which, in the preferred embodiment, comprises a neutral density optical filter 23. The neutral density filter 23 is a standard device made with a broad flat absorption spectrum sufficient to block light equally at all wavelengths in the infrared range of interest.

In operation, as the level of glucose changes, the light passing through the negative correlation filter 21 remains unaffected because it has already blocked all light in the glucose absorption bands. The intensity of the light passing through the neutral density filter 23 of the reference cell 22, on the other hand, will be reduced in proportion to glucose concentration. The difference in light intensity between the beams exiting the respective filters 21 and 23 is a measure of glucose concentration.

The intensities of the beams exiting the negative correlation filter 21 and neutral density filter 23 are measured, respectively, by photosensors 24 and 25. For the infrared bandwidth indicated above, a lead sulfide photodetector is preferred. The photosensors convert the measured light into signals representative of the light intensities, which signals are fed to a lock-in amplifier 26 which generates a signal representative of the difference in the measured intensities of the two beams. The differential signal is converted to digital form for input into a microprocessor 27 to calculate the actual glucose concentration. The concentration may be conveniently indicated by a suitable digital display 28. It should be noted that the modified light beams exiting the filters 21 and 23 could be directed to and utilize a single photosensor. This would help eliminate or reduce errors in drift.

When utilizing reflective measurements at longer wavelengths (in the range of 2700 to 3400 nm for glucose analysis, sensitivity may be substantially enhanced because of the stronger absorbance by glucose in this range. However, conventional optical fibers are not suitable for infrared transmission at these wavelengths and more expensive and fragile fibers, such as fluoride-based, are required. An alternate construction, eliminating the use of fiber optics, comprises a hand-held optical head which contains the light source, filters and photodectors.

Although the foregoing device and its method of operation were described with respect to the measurement of glucose concentration, other blood analytes such as cholesterol, triglycerides and uric acid may be similarly measured.

Figure 2:
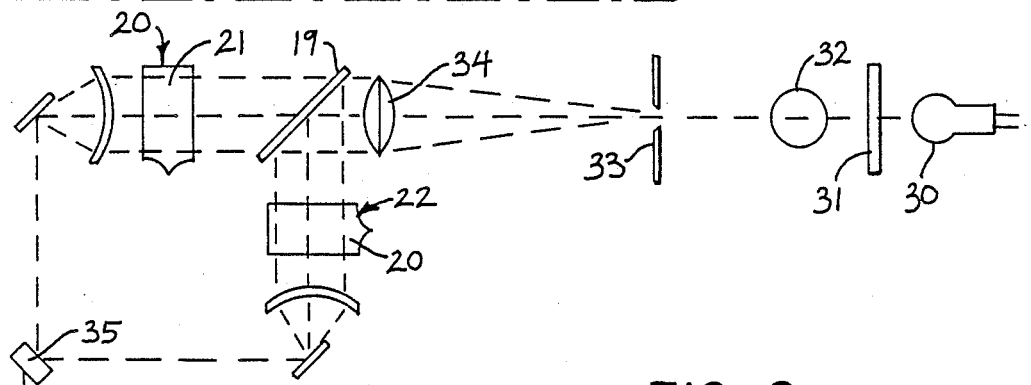
FIG. 2 is a schematic representation of an alternate embodiment of the invention.
Figure 2:
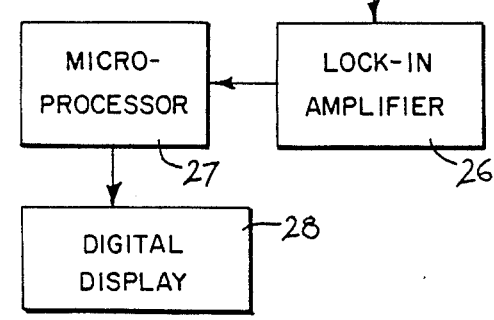

In FIG. 2, there is shown an alternate arrangement of an apparatus for the transmissive in vitro measurement of blood analytes. The basic principles of operation and analysis are the same as the apparatus for in vivo measurement using diffuse reflective or transmissive light in the preferred embodiment of FIG. 1, but with a few differences which will be discussed hereinafter.

A light source, such as a quartz halogen lamp 30, generates light in the near infrared range which, after passing through a diffuser 31, is directed transmissively through a sample 32 of human blood serum. Whole blood samples may also be used, but the instrument must be adjusted for higher light intensity and amplifier gain to penetrate the higher density whole blood. The serum (or blood) sample may be held in a conventional cuvette. Light exiting the serum sample 32 is passed through a slit 33 to eliminate stray light signals. For glucose measurement, the bandwidth should preferably range from 900 nm on the shorter wavelength end, where glucose absorbance becomes relatively higher, to about 1800 nm on the longer wavelength end, above which transmissive measurements are impractical due to the high absorbance by water.

The spectrally-modified light, as a result of its passage through the serum sample 32, is collimated by passage through lens 34 and directed into a beam splitter 19. The beam splitter 19, cells 20 and 22, photosensors 24 and 25, and the electronics for modifying the signals and computing the concentrations may be the same as in the preferred embodiment of FIG. 1. However, as previously suggested with respect to the description of the preferred embodiment, a single photosensor 35 may be substituted for the dual photosensors 24 and 25. With a single photosensor 35, the light paths from the cells 20 and 22 will have to be appropriately altered, as indicated. Furthermore, in order to provide the capability to discriminate between and separate the two light beams directed to the photosensor 35 and the signals produced thereby, the beam splitter 19 may be replaced with a mirror/chopper device (not shown) which would alternately direct the light from the sample to the correlation cell 20 and the reference cell 22. Alternatively, shutters could be interposed in the paths from the beam splitter for the same purpose.

The procedures for balancing either of the apparatus shown in FIG. 1 or FIG. 2, prior to making a measurement, are the same. In the in vivo version shown in FIG. 1, a reference cell 22 is positioned in the light path 13 in place of the ear 14. For the in vitro version shown in FIG. 2, a reference cell 22 is substituted for the sample cell 32. And, in either case, the output of the correlation cell channel is adjusted to provide a zero output from the amplifier 26. Next, a correlation cell 20 is substituted for the reference cell in the position of the ear 14 or sample 32, depending on the apparatus, and the output of the amplifier 26 is set at the glucose concentration value of the correlation cell. The apparatus is now balanced and ready for use. Although the water layers used with the reference and correlation cells have less absorbance than whole blood or blood serum, this difference in absorbance affects both channels equally and cancels out. Thus, when actual samples are run, the only difference in the output of the two channels will be as a result of the glucose in the sample.

For the analysis of blood analytes other than glucose, an appropriate negative correlation filter would have to be substituted. As in the case of glucose measurement, the substitute filter requires an absorption spectra for the analyte to be measured which is sufficient to block light in the selected bandwidth for the maximum expected concentration of that analyte.

In lieu of a neutral density filter 23, in either of the foregoing embodiments, the reference cell 22 may comprise a compensator cell having a spectrum equivalent to a high level of all of the encountered interference. A compensator cell would respond only to changes in the analyte of interest and not to changes in the interferring substances. An alternate approach to compensating for interferring analytes utilizes an interference cell ahead of the sample source, e.g. serum sample 32 in FIG. 2. Like a compensator cell, an interference cell would contain the spectra of the potentially interfering substances sufficient to block light in the interfering absorption bands.

The correlation techniques useful in determining the concentration of glucose or other blood serum analytes described herein provide significant advantages over prior art methods of near infrared analysis based on measurement of absorbance at single or multiple specific wavelengths. The method and apparatus described use information over the entire bandwidth of interest and are limited only by the bandwidth of the photosensor. This substantially enhances the sensitivity of the instrument. An equally important advantage of the disclosed correlation technique is its insensitivity to changes in overall infrared absorbance caused by factors which are unrelated to concentration of the analyte being measured. Varying skin and other tissue characteristics can produce significant variations in the overall near infrared absorbance levels. However, in the disclosed method, these variations are not significant because they cancel out in differencing the signals from the correlation cell and reference cell.

Various modes of carrying out the invention are contemplated as being within the scope of the following claims particularly pointing out and distinctly claiming the subject matter which is regarded as the Invention.

I claim:

1. A method for the non-invasive measurement of the concentration of a blood analyte comprising the steps of:

(a) directing a beam of near infrared light to a source containing the blood analyte to be measured;

(b) causing the beam to be transmitted or reflected by the source so as to provide a spectrally-modified beam;

(c) directing the modified beam into two paths;

(d) directing the modified beam of one path through a first optical filter having an absorption spectra of the analyte sufficient to block light for the maximum expected concentration of the analyte;

(e) directing the modified beam of the other path through a second optical filter having an absorption spectra sufficient to block light equally at all wavelengths;

(f) measuring the relative intensity of the beam from each path exiting its respective optical filter;

(g) generating a signal representative of the difference in intensity between the beams; and, (h) converting the signal into an indication of analyte concentration.

2. The method as set forth in claim 1 wherein the first optical filter comprises a solution of the analyte applied to a glass substrate.

3. The method as set forth in claim 1 wherein the analyte is glucose.

4. The method as set forth in claim 3 wherein the near infrared light includes wavelengths in the range of 1800 to 3400 nm and is spectrally modified by reflectance from the source.

5. The method as set forth in claim 3 wherein the near infrared light includes wavelengths in the range of 900 to 1800 nm and is spectrally modified by transmission through the source.

6. The method of claim 1 wherein said source is human tissue and including the step of locating said human tissue is said beam.

7. The method of claim 6 wherein said human tissue has a skin surface layer and said spectrally-modified beam is diffusively reflected from the skin surface layer of the human tissue.

8. The method of claim 6 wherein the light is spectrally modified by transmission through the tissue.

9. The method of claim 8 wherein the analyte is glucose, and selecting said infrared light to detect said glucose.

10. The method of claim 1 including locating a blood serum specimen in said beam as the source and transmitting the light through the blood serum specimen.

11. The method as set forth in claim 10 including selecting said light to have a wavelength to detect an analyte selected from the group consisting of glucose, cholesterol, triglycerides, and uric acid.

12. Apparatus for the non-invasive measurement of the concentration of a blood analyte comprising a source of modulated near infrared light, means for transmitting the light to a blood analyte source containing the blood analyte and for retransmitting spectrally-modified light from the blood analyte source, means for directing the spectrally-modified light into two beams, a first optical filter in the path of one modified beam having an absorption spectra of the analyte sufficient to block light for the maximum expected concentration of the analyte, a second optical filter in the path of the other modified beam having an absorption spectra sufficient to block light equally at all wavelengths, photosensor means in the path of each beam exiting its respective optical filter for converting the light into a signal representative of the intensity of each beam, means for generating a signal representative of the difference in the intensities of the beams, and means for converting the signal representative of the difference into an of analyte concentration.

13. The apparatus as set forth in claim 12 wherein the light transmitting and retransmitting means comprises a fiber optic-linked optrode.

14. The apparatus as set forth in claim 13 wherein the infrared light includes wavelengths in the range of 1800 to 3400 nm.

15. The apparatus as set forth in claim 14 wherein the photosensor means comprises a lead sulfide photodetector.

16. The apparatus as set forth in claim 12 wherein the infrared light includes wavelengths in the range of 900 to 1800 nm.

17. The apparatus as set forth in claim 12 wherein the means for directing the spectrally-modified light into two beams comprises a beam splitter.

18. Apparatus for non-invasive measurement of glucose concentration in human body tissue comprising a source of modulated near infrared light, means for reflectively transmitting the light to the skin surface of the tissue and retransmitting spectrally-modified light diffusely-reflected from the skin surface, means for receiving and directing the spectrally-modified light into two beam paths, a negative correlation filter in one of the paths having a glucose absorption spectra sufficient to block light for the maximum anticipated concentration of glucose, a neutral density filter in the other path having an absorption spectral sufficient to block light equally at all wavelengths, photosensor means for receiving the filtered beams and for converting the same into signals representative of the intensities of the filtered beams, a lock-in amplifier connected to said photosensor means for generating a signal representative of the difference in the intensities of the filtered beams, and a microprocessor connected to said amplifier for calculating the glucose concentration from the differential signal.

19. The apparatus as set forth in claim 18 wherein the means for reflectively transmitting and retransmitting the light comprises a fiber optic-linked optrode.

20. The apparatus as set forth in claim 19 wherein the means for receiving and directing the modified light comprises a beam splitter.

21. The apparatus as set forth in claim 20 wherein the photosensor means comprises a photodetector for each beam.

* * * * *